United States Patent [19]

Bornengo et al.

[11] Patent Number: 4,954,643

[45] Date of Patent: Sep. 4, 1990

[54] PROCESS FOR PREPARATION OF PERFLUOROPROPANE OXIDE

[76] Inventors: Giorgio Bornengo, 8, via Paletta; Filippo M. Carlini, 7, C.so Torino; Michele Pontevivo, 4, via Monte Nero; Giorgio Bottaccio, 16, via Manin, all of Novara, Italy

[21] Appl. No.: 306,262

[22] Filed: Jan. 31, 1989

Related U.S. Application Data

[63] Continuation of Ser. No. 902,078, Aug. 28, 1986, abandoned, which is a continuation of Ser. No. 674,920, Nov. 26, 1984, abandoned.

[30] Foreign Application Priority Data

Nov. 28, 1983 [IT] Italy .................. 23908 A/83

[51] Int. Cl.$^5$ .......................................... C07D 303/00
[52] U.S. Cl. .................................................. 549/531
[58] Field of Search ............................. 549/531, 525

[56] References Cited

U.S. PATENT DOCUMENTS

| | | | |
|---|---|---|---|
| 3,358,003 | 12/1967 | Eleuterio et al. | 549/531 |
| 3,992,432 | 11/1976 | Napier et al. | 549/531 |
| 4,286,068 | 8/1981 | Mares et al. | 549/531 |
| 4,433,179 | 2/1984 | Lohse et al. | 548/341 |
| 4,562,276 | 12/1985 | Venturello et al. | 549/531 |

FOREIGN PATENT DOCUMENTS

| | | | |
|---|---|---|---|
| 64293 | 11/1982 | European Pat. Off. | 549/521 |
| 2055821 | 3/1981 | United Kingdom . | |

OTHER PUBLICATIONS

D. Landini et al, Gazzetta Chimica Italiana, vol. 105, (1975), pp. 863–874.

C. Venturello et al., Jour. Org. Chem., (1983), vol. 48, pp. 3833–3835.

*Primary Examiner*—Mark L. Bell
*Assistant Examiner*—David M. Brunsman
*Attorney, Agent, or Firm*—Morgan & Finnegan

[57] ABSTRACT

An improved process for the preparation of perfluoropropene oxide by the reaction of perfluoropropene with hydrogen peroxide in an aqueous alkaline medium is described. The improved process is characterized by carrying out the reaction in the presence of a phase-transfer catalyst selected from the group consisting of quaternary ammonium salts, phosphonium salts, and lipophilic complexing agents for cations, and by carrying out the addition of an aqueous solution of an inorganic base to the reaction mixture gradually so that a constant reaction temperature between $-10°$ C. and $-60°$ C. is maintained.

12 Claims, No Drawings

PROCESS FOR PREPARATION OF PERFLUOROPROPANE OXIDE

This is a continuation of application Ser. No. 06/902,078, filed Aug. 28, 1986, now abandoned, which is a continuation of application Ser. No. 06/674,920, filed Nov. 26, 1984, now abandoned.

BACKGROUND OF THE INVENTION

From the teaching of U.S. Pat. No. 3,358,003 it is known that perfluoropropene oxide can be obtained by reacting the perfluoropropene with an aqueous alkaline solution of hydrogen peroxide which may contain an organic water-miscible solvent.

However, using this process only low yields of perfluoropropene oxide (e.g., 30%) and low degrees of selectivity (e.g., 35%) are obtained under the most favorable conditions. In addition, considerable quantities of fluorinated by-products soluble in the aqueous phase result from secondary reactions of the perfluoropropene and from subsequent decomposition in the aqueous alkaline medium of the perfluoropropene oxide thus formed.

Moreover, in this process it is necessary to maintain the conversion values so that they do not exceed 90% because the selectivity for the formation of perfluoropropene oxide decreases at conversion values between 90% and 100%.

OBJECTS OF THE INVENTION

The objects of the present invention include the oxidation of perfluoropropene with hydrogen peroxide at high conversion values (greater than 90%) and high selectivities, and consequently resulting in yields of perfluoropropene oxide (greater than 60%) with a minimum amount of fluorinated by-products derived from secondary reactions of the perfluoropropene or from the decomposition of the perfluoropropene oxide in the aqueous alkaline medium.

GENERAL DESCRIPTION OF THE INVENTION

It has now been found that the above indicated objects are achieved when the oxidation of the perfluoropropene with alkaline hydrogen peroxide is carried out in the presence of a phase-transfer catalyst and when the addition of an aqueous solution of an inorganic base to the reaction mixture is carried out gradually, thus maintaining a constant reaction temperature at a value between $-10°$ and $-60°$ C.

SPECIFIC DESCRIPTION OF THE INVENTION

The present invention relates to a process for the preparation of perfluoropropene oxide by the oxidation of perfluoropropene with hydrogen peroxide in an aqueous alkaline medium, optionally in the presence of a water-miscible organic solvent. To a mixture consisting of perfluoropropene, an aqueous solution of hydrogen peroxide, a water-miscible organic solvent, optionally an inert organic solvent substantially immiscible with water, and a phase-transfer catalyst selected from the group consisting of quaternary ammonium salts, quaternary phosphonium salts, and lipophilic complexing agents for cations, maintained at a temperature between $-10°$ and $-60°$ C. with stirring, is gradually added an aqueous solution of an inorganic base. The addition is carried out gradually, over a period of time between 15 minutes and 6 hours to maintain the temperature constant.

The volume ratio of the organic phase (perfluoropropene, catalyst and optionally water-immiscible organic solvent) to the aqueous phase (aqueous solution of hydrogen peroxide, water-miscible organic solvent, and basic aqueous solution) in the reaction mixture is not critical and may preferably vary between 0.01 and 5.

Hydrogen peroxide is added to the reaction mixture in amounts between 1 to 10 moles per mole of perfluoropropene, preferably between 3 and 5 moles per mole of perfluoropropene. It is normally added as a 35% aqueous solution.

Suitable inorganic bases may be chosen from amongst the hydroxides and the basic salts of alkaline metals, alkaline earth metals and ammonium, such as for example, sodium hydroxide, potassium hydroxide, ammonium hydroxide, sodium bicarbonate, and sodium acetate.

The base is added to the reaction system as an aqueous solution in amounts between 0.01 and 10 moles per mole of perfluoropropene.

By adjusting the molar ratio of base to perfluoropropene, it is possible to obtain the desired degree of conversion. For instance with a molar ratio of 1-1.2 a conversion of about 90% is achieved, while with a ratio of 2-2.5 a conversion nearing 100% is attained.

As water-miscible organic solvents there may be used aliphatic alcohols, ketones, aldehydes and esters, in particular methanol, ethanol, acetone and acetaldehyde.

The quantity to be employed is not critical and depends on the reaction conditions.

Their use permits the reaction to be carried out at low temperatures, for example between $-30°$ and $-50°$ C.

Preferably the substantially water immiscible organic solvent has a freezing point below $-60°$ C., or at least lower than the reaction temperature. However, the perfluoropropene, perfluoropropene oxide and catalyst must be sufficiently soluble in the solvent.

The presence of the solvent minimize secondary reactions of the perfluoropropene oxide in the aqueous alkaline phase and consequently result in an increased yield.

The solvent may be used in amounts of between 0.1 and 20 moles per mole of perfluoropropene. The amount chosen will depend on the solvent's immiscibility with the aqueous phase and the solubility of the catalyst, perfluoropropene, and perfluoropropene oxide in the solvent.

Suitable solvents include, for example, ethers such as di-iso-propyl and di-n-butyl ether; halogenated compounds such as carbon tetrachlordide, 1,2-dichloroethane, methylene chloride, chloroform; chloro-fluorocarbons such as 1,2-dichloro-1,1,2,2-tetrafluoroethane, 1,1,2-trichloro-1,2,2-trifluoroethane, 1,1,2,2-tetrachloro-1,2-difluoroethane; fluorocarbons such as perfluorocyclobutane, perfluorodimethylcyclobutane, perfluorohexane and hexafluorobenzene.

Particularly preferred are the solvents in which both the perfluoropropene and the perfluoropropene oxide are highly soluble, such as the chloro-fluoro-hydrocarbons, as well as solvents in which the catalyst is highly soluble, such as the chlorinated compounds.

The phase-transfer catalysts, which are selected from the group consisting of the quaternary ammonium salts, the quaternary phosphonium salts, and the lipophilic complexing agents for cations, preferably must have good solubility in the organic phase. They are used in amounts comprised between 0.001 moles and 10 moles per mole of perfluoropropene.

The quaternary ammonium or phosphonium salts useful in the present invention are represented by the following general formulae:

 (I)

 (II)

where $R_1$, $R_2$, $R_3$ and $R_4$ may be the same as or different from each other and where each represents a hydrocarbon group which may or may not be substituted by a functional group inert under the reaction conditions. The type and the length of the hydrocarbon group are chosen with a view to their solubility in the organic phase, to the composition of the reaction mixture, and to the desired reaction rate.

Examples of such hydrocarbon groups include alkyl, alkenyl, cycloalkyl, cycloalkenyl, aryl, aralkyl, and alkenaryl groups.

Particularly preferred are the alkyl, aryl, and arylalkyl groups.

As far as the length of the hydrocarbon chain is concerned, the total number of carbon atoms contained in $R_1$, $R_2$, $R_3$ and $R_4$ usually is between 6 and 100, preferably between 10 and 50.

In the hydrocarbon chain there may be present inert functional groups such as halogens, acyl, carboxy, and ester groups.

$R_1$, $R_2$, $R_3$ and $R_4$ may combine with each other to form a nitrogen containing heterocylic ring or they may form part of a polymeric compound.

Quarternary ammonium ions that may be conveniently used include the following: tetraethylammonium, tetra-n-propylammonium, tetra-n-butylammonium, tri-n-octyl-methylammonium, cetyl-trimethylammonium, benzyl-trimethylammonium, benzyl-triethylammonium, cetyl benzyl-dimethylammonium, cetylpyridinium, n-dodecyl-pyridinium, phenyl-trimethyl ammonium, phenyl-triethyl-ammonium, N-benzyl-picolinium, and 2-6-di-tert-butyl pyridinium.

The preferred ions are those having alkyl groups with a long chain and pyridinium ions.

Phosphonium ions that may be conveniently used include the following: tetraethylphosphonium, tetra-n-butylphosphonium, tri-n-octylethylphosphonium, cetyl-triethylphosphonium, cetyl-tri-n-butylphosphonium, n-butyl-triphenyl-phosphonium, n-amyl-triphenylphosphonium, n-hexyl-triphenyphosphonium, n-heptyl-triphenylphosphonium, methyl-triphenylphosphonium, benzyl-triphenylphosphonium, tetraphenyl phosphonium, and aceto[nyl]-triphenyl phosphonium.

The preferred phosphonium ions have alkyl groups with a long chain as well as those carrying three phenyl groups.

The $X^-$ ions in formulae (I) and (II) are not subject to particular limitations. They may be conveniently halogen ions, ions from other mineral acids, ions from organic acids, and hydroxy ions.

Examples of such ions include chloride, bromide, iodide, fluoride, hydrogen sulphate, sulphate, nitrate, phosphate, perchlorate, hydroxy, acetate, benzoate, benzenesulphonate and p-toluene-sulphonate. Amongst these the chloride and the hydroxy are ions preferred.

The lipophilic complexing agents for cations are chosen from compounds which, besides showing a certain solubility in the organic phase, are capable of forming stable complexes with the cations present in the reaction mixture.

Typical compounds which may be used in the present invention are represented by the oxygenated ring-shaped compounds, commonly called "crown ethers", and by polyethyleneglycol or derivates therefrom.

The "crown ethers", described for instance in Pedersen, Jn. of Amer. Chem. Soc., 8%, 2495, 7017 (1967), have the capacity of forming stable coordination complexes with alkaline and alkaline earth metal ions. They may almost totally be represented, also including their substituted derivates, by the general formula:

 (III)

where n is an integer between 4 and 20 and where a in each of the n-groups $(CH_2)_a$ may be the same or different values and may be from 2, 3 and 4.

Examples of some of the "crown ethers" (in accordance with the Pederson nomenclature) which may be used in this invention are as follows:

18-crown-6, dicyclohexyl-18-crown-6, dibenzo-18-crown-6, benzo-15-crown-5, dibenzo-15-crown-5, dibenzo-21-crown-7, dibenzo-24-crown-8, dibenzo-30-crown-10, dicyclohexyl-24-crown-8. The polyethyleneglycols that may be used according to the present invention may be polymerized to various degrees.

Polyethyleneglycol derivate that may be used according to the present invention include compounds represented by formulae (IV) and (V), their substituted derivatives, the copolymers of ethylene oxide with other monomers, and in general the compounds containing the structure of the polyethyleneglycol. In the following formulae $$R_4-O-(CH_2-CH_2)_t-H \quad (IV)$$

$$R_5-O-(CH_2-CH_2-O)_u-R_6 \quad (V)$$

t is an integer greater than or equal to 5, u is an integer greater than or equal to 3, $R_4$, $R_5$ and $R_6$ are substituted or unsubstituted hydrocarbon groups containing from 1 to 80 carbon atoms.

The preferred polyethyleneglycols are alkyl-phenyl-polyethyleneglycol (TRITON X 100 ®), polyethylene-lauryl ether (BRIJ 35 ®), and derivatives of the formula:

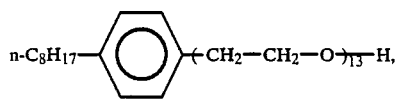

-continued

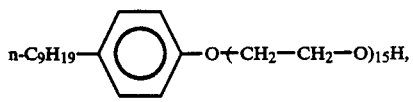

CH$_3$O(CH$_2$—CH$_2$—O)$_3$CH$_3$ n-C$_4$H$_9$O(CH$_2$=CH$_2$—O)$_{10}$-n-C$_4$H$_9$

The reaction temperature is not critical and may be within a range between −10° and −60° C., depending on the composition of the reaction mixture and on the desired reaction rate.

At the end of the reaction, the organic phase is separated from the aqueous phase and the perfluoropropene oxide is isolated from the organic phase, by simple separation techniques, for instance by distillation.

The process of the present invention, contrary to the process of the prior art permits the preparation of perfluoropropene oxide at high selectivities and at high conversion rates with a good control of the reaction, thus avoiding decomposition of the perfluoropropene oxide as well as minimizing the formation of by-products.

It is thus possible, operating at high conversion rates, to avoid the long and costly steps of separating perfluoropropene oxide from the unreacted perfluoropropene, as well as avoid the recycling of perfluoropropene, thus resulting in operational and economic advantages.

Thus, the present process allows the preparation of perfluoropropene oxide in high yields by means of a simplified and inexpensive procedure suitable for use on a commercial scale.

The process of the present invention may be usefully extended to the preparation of oxides of other perfluorinated alkenes.

The following examples are provided to illustrate the invention and are not to be used to limit the scope of the invention.

EXAMPLE 1

Into a 2.5 l reactor, fitted with a thermostatically controlled cooling sleeve with the forced circulation of a refrigerating mixture (CH$_3$—CO—CH$_3$+solid CO$_2$) and provided with a stirrer, were loaded 297 g of methanol, 289 g of a 36% hydrogen peroxide solution and 1.8 g (4.5 mmols) of tetrabutyl-ammonium hydroxide (as a phase transfer catalyst) dissolved in 132 g of methylene chloride.

The reactor was then cooled to −50° C. and into it were then introduced 100 g of perfluoropropene.

Thereupon, by means of a dropping funnel and with vigorous stirring, there was added over a period of time of about 90 min., into the mixture a solution consisting of 40 g of KOH in 80 ml of H$_2$O. The reaction was then completed while maintaining this mixture under constant stirring for 3 hours at −50° C.

Then, by raising slowly the temperature from −50° C. to +20° C., the gas was removed from the reactor and separated from the organic solvent by means of a condenser maintained at −20° C. The perfluoropropene oxide was then collected in a trap cooled to −70° C.

Gas chromatographic analysis showed that the final gaseous mixture contained 86% perfluoropropene oxide, with a conversion of perfluoropropene of 95%, a selectivity of 74%, and a yield of perfluoropropene oxide of 70%.

EXAMPLES 2–12

The same procedures as that followed in Example 1 was repeated, except that instead of tetrabutylammonium hydroxide, 4.5 mmols of the phase-transfer catalysts reported on Table 1 were used.

The conversions and yields obtained are recorded on Table 1.

TABLE 1

| Example No. | Catalyst | Conversion of Perfluoropropene | Selectivity in perfluoropropene oxide |
|---|---|---|---|
| 2 | (C$_8$H$_{17}$)$_3$CH$_3$NCl | 93 | 66 |
| 3 | (C$_4$H$_9$)$_4$NCl | 91 | 62 |
| 4 | (C$_3$H$_7$)$_4$NOH | 80 | 70 |
| 5 | (C$_2$H$_5$)$_4$N Cl | 92 | 52 |
| 6 | (C$_2$H$_5$)$_4$NI | 94 | 50 |
| 7 | (CH$_3$)$_3$(C$_6$H$_5$CH$_2$)NOH | 92 | 56 |
| 8 | (CH$_3$)$_3$(C$_6$H$_5$CH$_2$)NCl | 95 | 48 |
| 9 | (C$_6$H$_5$)$_3$(CH$_3$—CO—CH$_2$)PCl | 90 | 55 |
| 10 | (C$_4$H$_9$)$_4$PCl | 93 | 57 |
| 11 | dibenzo-18-crown-6 | 88 | 70 |
| 12 | [piperidinium derivative] Cl$^-$ | 99 | 68 |

EXAMPLE 13

The preparation of Example 1 was repeated, but 7 grams of polyoxyethylenelaurylether (BRIJ 35 ®) instead of tetrabutylammoniumhydroxide was used as the phase-through catalyst.

The conversion of perfluoropropene was 80% and the selectivitY for the preparation of perfluoropropene oxide was 65%.

EXAMPLE 14

The procedure of Example 1 was repeated but 7 g of alkylphenylpolyethylenglycol (TRITON X 100) was used as the phase-transfer catalyst.

The resulting conversion was 82% and the selectivity was 66%.

EXAMPLE 15

The procedure of Example 2 was repeated but 156 g. of 1,1,2 trichloro-1,2,2-trifluoroethane (FREON 113) was used instead of 132 g of methylene chloride. The conversion was 84% and the selectivity was 66%.

EXAMPLE 16

The procedure of Example 12 was repeated except that 156 g of 1,1,2-trichloro 1,2,2-trifluoroethane was used instead of 132 g of methylene chloride. The conversion was 98% and the selectivity was 65%.

EXAMPLE 17

(Comparison)

The procedure of Example 1 was repeated except that neither the phase-transfer catalyst nor the organic solvent immiscible with the aqueous phase, i.e., the methylene chloride, were used.

Gas-chromatographic analysis showed that the gaseous phase contained 77% perfluoropropene oxide, with a conversion of 86%, a selectivity of 44%, and a yield of 38%.

What we claim is:

1. A process for the preparation of perfluoropropene oxide by:
   (A) mixing perfluoropropene with an inert organic solvent substantially immiscible with water, an aqueous solution of hydrogen peroxide, an organic water miscible solvent, and a phase transfer catalyst selected from the group consisting of quaternary ammonium salts, quaternary phosphonium salts, and lipophilic complexing agents for cations at a temperature between $-10°$ C. to $-60°$ C.; and
   (B) gradually adding to the mixture with stirring an aqueous solution of an inorganic base over a period of time from between 15 minutes to 6 hours, the rate of addition being chosen so as to maintain the temperature of the reaction mixture constant.

2. Process according to claim 1, characterized in that the hydrogen peroxide is present in the mixture in an amount between 1 and 10 moles per mole of perfluoropropene.

3. Process according to claim 1, characterized in that the hydrogen is present in the mixture in an amount between 3 and 5 moles per mole of perfluoropropene.

4. Process according to claim 1, characterized in that the inorganic base is added in an amount between 0.01 and 10 moles per mole of perfluoropropene.

5. Process according to claim 1, characterized in that the organic water-miscible solvent is selected from the group consisting of methanol, acetone, and acetaldehyde.

6. Process according to claim 1, characterized in that the organic solvent immiscible with water is present in the mixture in an amount between 0.1 and 20 moles per mole of perfluoropropene.

7. Process according to claim 1, characterized in that the organic solvent immiscible with water is selected from the group consisting of chlorinated compounds and fluorinated-chlorinated hydrocarbons.

8. Process according to claim 1, characterized in that the phase-transfer catalyst is present in the mixture in an amount between 0.001 and 10 moles per mole of perfluoropropene.

9. Process according to claim 1, characterized in that the quaternary ammonium and phosphonium salts contain from 6 to 100 carbon atoms.

10. Process according to claim 1, characterized in that the lipophilic complexing agent is selected from the group consisting of oxygenated cyclic compounds of the formula:

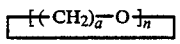

where n is an integer between 4 and 20 and where a in each of the n-groups $(CH_2)_a$ may have values equal to or different from each other and may be 2, 3 or 4.

11. Process according to claim 1, characterized in that the lipophilic complexing agent is polyethyleneglycol or derivatives thereof.

12. Process according to claim 1, characterized in that the ratio by volume between the organic phase and the aqueous phase present in the reaction mixture is between 0.01 and 5.

* * * * *

UNITED STATES PATENT AND TRADEMARK OFFICE
CERTIFICATE OF CORRECTION

PATENT NO. : 4,954,643
DATED : September 4, 1990
INVENTOR(S) : Bornengo et al.

It is certified that error appears in the above-identified patent and that said Letters Patent is hereby corrected as shown below:

On the title page, in item [54] and in column 1, in the title,

"PERFLUOROPROPANE" should read -- PERFLUOROPROPENE --.

Column 4, line 7, delete "ions" between "are" and "perferred", and insert --ions-- between "hydroxy" and "are".

line 50, delete "--(V)" at the end of the formula "$R_5-O-(CH_2-CH_2-O)_u-R_6$" and insert at the end of the line --(V)--.

Column 6, line 60, "selectivitY" should read --selectivity--.

line 66, insert $^r$ after "(TRITON X 100)".

UNITED STATES PATENT AND TRADEMARK OFFICE
CERTIFICATE OF CORRECTION

PATENT NO. : 4,954,643

DATED : September 4, 1990

INVENTOR(S) : Bornengo et al.

It is certified that error appears in the above-identified patent and that said Letters Patent is hereby corrected as shown below:

Column 7, line 4, insert $^r$ after "(FREON 113)".

Signed and Sealed this

Twenty-first Day of April, 1992

*Attest:*

HARRY F. MANBECK, JR.

*Attesting Officer*    *Commissioner of Patents and Trademarks*